(12) United States Patent
Dehkordi et al.

(10) Patent No.: US 11,402,335 B2
(45) Date of Patent: Aug. 2, 2022

(54) FIBER BLEND IDENTIFICATION AND RATIO MEASUREMENT

(71) Applicant: Uster Technologies AG, Uster (CH)

(72) Inventors: Peyman Dehkordi, Knoxville, TN (US); Kent A. Rinehart, Knoxville, TN (US); Weichang C. Zhao, Oak Ridge, TN (US)

(73) Assignee: Uster Technologies AG, Uster (CH)

( * ) Notice: Subject to any disclaimer, the term of this patent is extended or adjusted under 35 U.S.C. 154(b) by 208 days.

(21) Appl. No.: 16/644,845

(22) PCT Filed: Sep. 11, 2018

(86) PCT No.: PCT/CH2018/000038
§ 371 (c)(1),
(2) Date: Mar. 5, 2020

(87) PCT Pub. No.: WO2019/051620
PCT Pub. Date: Mar. 21, 2019

(65) Prior Publication Data
US 2021/0199593 A1 Jul. 1, 2021

Related U.S. Application Data (60) Provisional application No. 62/558,506, filed on Sep. 14, 2017.

(51) Int. Cl.
*G01N 21/89* (2006.01)
*D06H 3/16* (2006.01)
*G01N 33/36* (2006.01)

(52) U.S. Cl.
CPC ......... *G01N 21/8915* (2013.01); *D06H 3/165* (2013.01); *G01N 33/365* (2013.01)

(58) Field of Classification Search
CPC .. G01N 21/8915; G01N 33/365; D06H 3/165; D06H 3/00; D01G 31/006; D01H 13/32
See application file for complete search history.

(56) References Cited

U.S. PATENT DOCUMENTS

| 5,270,787 A | 12/1993 | Uster |
| 5,311,290 A | 5/1994 | Olson et al. |

(Continued)

FOREIGN PATENT DOCUMENTS

| EP | 0652432 | 5/1995 |
| GB | 2095828 B | 12/1985 |

(Continued)

*Primary Examiner* — Sang H Nguyen
(74) *Attorney, Agent, or Firm* — Luedeka Neely Group, P.C.; Rick Barnes (57) ABSTRACT

An instrument for identifying at least one of fiber blend composition and fiber blend ratio in an input material moved by a third set of fiber movements. A second spectral radiation source directs radiation toward the input material. A second spectral sensor receives portions of the second radiation that pass through the input material. A third spectral sensor receives portions of the second radiation that reflect off of the input material. A controller processes the signals from at least one of the second spectral sensor and the third spectral sensor to determine at least one of the fiber blend composition and the fiber blend ratio in the input material. The controller also sends control signals to the second electromagnetic radiation source and the third set of fiber movements.

20 Claims, 5 Drawing Sheets

(56) References Cited

U.S. PATENT DOCUMENTS

| | | | |
|---|---|---|---|
| 5,321,496 A | 6/1994 | Shofner et al. | |
| 5,355,561 A | 10/1994 | Rieter | |
| 5,367,747 A | 11/1994 | Uster | |
| 5,383,017 A * | 1/1995 | Schurch | G01N 21/8915 356/238.3 |
| 5,414,520 A * | 5/1995 | Joss | B65H 63/065 356/238.3 |
| 5,420,439 A * | 5/1995 | Landwehrkamp | G01N 21/8915 242/364.11 |
| 5,483,844 A | 1/1996 | Uster | |
| 5,491,876 A | 2/1996 | Uster | |
| 5,530,551 A | 6/1996 | Cantrall et al. | |
| 5,533,145 A * | 7/1996 | Shofner | G01N 21/8915 209/576 |
| 5,594,544 A | 1/1997 | Horiuchi et al. | |
| 5,786,894 A | 7/1998 | Shields et al. | |
| 5,991,046 A * | 11/1999 | Shakespeare | G01N 21/8901 356/429 |
| 6,407,819 B1 | 6/2002 | Rieter | |
| 6,967,721 B2 * | 11/2005 | Moshe | G01N 21/47 356/237.1 |
| 7,307,729 B2 * | 12/2007 | Moshe | A24C 5/3412 356/430 |
| 7,418,767 B2 | 9/2008 | Premier | |
| 7,880,156 B2 * | 2/2011 | Shakespeare | G01N 21/8903 250/559.4 |
| 9,180,653 B2 * | 11/2015 | Minamida | B29C 70/54 |
| 2003/0107729 A1 * | 6/2003 | Furter | G01N 21/8915 356/238.1 |
| 2004/0156044 A1 * | 8/2004 | Pirani | D06H 3/08 356/238.3 |
| 2006/0010655 A1 | 1/2006 | Schlichter | |
| 2016/0077019 A1 * | 3/2016 | Mathon | B65H 26/02 356/238.1 |

FOREIGN PATENT DOCUMENTS

| | | |
|---|---|---|
| WO | 9313407 A1 | 7/1993 |
| WO | 1993013407 | 7/1993 |
| WO | 1995029396 | 11/1995 |
| WO | 2000008448 | 8/1999 |
| WO | 2010009565 | 1/2010 |

* cited by examiner

Fig. 6

FIBER BLEND IDENTIFICATION AND RATIO MEASUREMENT

FIELD

This invention relates to the field of textile fiber characteristic measurement. More particularly, this invention relates to measurement of blended textile fiber characteristics. Even more particularly, it relates to a measurement instrument for identifying fiber blend composition and/or fiber blend ratio in an input material comprising fibers, and to a method for identifying fiber blend composition and/or fiber blend ratio in an input material comprising fibers.

BACKGROUND

Textile fiber is the raw material for making textiles or textile intermediate products, such as yarn and fabric. Historically, cotton and other natural fibers have been the most important and utilized textile raw material. In recent years, however, synthetic or manmade fibers have gained popularity and utilization. As the name implies, synthetic fibers such as polyester and rayon are made artificially using chemical process.

One of the most basic textile processes is converting fibers into yarn which is typically performed by spinning mills. A typical spinning mill may process only cotton fiber, only manmade fiber, or a blended combination of natural/manmade or manmade/manmade fibers (blends). Blends may offer a cost and performance advantage that might not be matched by cotton alone for a given application. In such case, the choice of fiber type and the ratio of different fibers types (blend ratio) in the blend plays an important role in cost and performance of the yarn produced.

Therefore, material type and blend ratio are important parameters to maintain, monitor, and control in processing facilities such as a spinning mill. The current blend ratio measurement method is based on chemical techniques where a blend sample is initially weighed and then weighed again, sometimes iteratively so, after chemically removing each of the blend components one at a time (in those cases where more than one additional component is present). This is an offline and time-consuming method.

U.S. Pat. No. 5,355,561 describes measuring a characteristic of a sliver to determine fiber blend. However, the fibers must be compressed at the location where they pass a commercially available measuring instrument.

U.S. Pat. No. 5,270,787 describes electro-optical measurement of individual entities in fibers that are delivered one at a time to a fluid stream. Each fiber is generally parallel with the direction of fluid flow. A sensor senses data such as the speed of the entity, length, fiber ribbon width, fineness, cross-sectional area, maturity, cross-sectional circularity, shape, surface roughness, etc. Optical filtering provides information about composition (natural or man-made) and appearance (color and polarization). However, additional, simpler, or other characteristics of fiber blend composition are desired.

SUMMARY

What is needed, therefore, is a measurement instrument and a method for identifying fiber blend composition and/or fiber blend ratio that address issues such as those described above, at least in part.

The above and other needs are met by a measurement instrument and a method for identifying fiber blend composition and/or fiber blend ratio in an input material comprising fibers according to the independent claims. Advantageous embodiments are defined in the dependent claims.

The measurement instrument according to the invention has a sample sensing module and a control module.

The sample sensing module comprises a third set of fiber movements for drawing the input material through the sample sensing module at a second speed. The sample sensing module further comprises a second electromagnetic radiation source disposed on an adjacent side of the input material for directing a second beam of electromagnetic radiation toward the input material at a second location within the sample sensing module, the second beam of electromagnetic radiation containing at least two clearly distinct wavelengths of the electromagnetic spectrum. The sample sensing module further comprises a second electromagnetic radiation sensor disposed on an opposite side of the input material opposite the second electromagnetic radiation source such that the second electromagnetic radiation sensor can receive second transmitted portions of the second beam of electromagnetic radiation that pass through the input material, and/or a third electromagnetic radiation sensor disposed on a same side of the input material as the second electromagnetic radiation source such that the third electromagnetic radiation sensor can receive third reflected portions of the second beam of electromagnetic radiation that reflect off of the input material, wherein the second and/or the third electromagnetic radiation sensor are each configured to receive electromagnetic radiation at at least two clearly distinct wavelengths of the electromagnetic spectrum.

The control module comprises a controller configured for receiving data signals from the second electromagnetic radiation sensor and/or the third electromagnetic radiation sensor, sending control signals to the second electromagnetic radiation source and the third set of fiber movements, and processing the data signals from the second electromagnetic radiation sensor and/or the third electromagnetic radiation sensor to determine the fiber blend composition and/or the fiber blend ratio in the input material.

In one embodiment, the measurement instrument according to the invention further comprises a sample preparation module for receiving and preparing the input material. The sample preparation module comprises a first set of fiber movements for receiving the input material and providing the input material at a first speed that is less than or equal to the second speed The sample preparation module further comprises a second set of fiber movements for receiving the input material from the first set of fiber movements at the first speed and providing the input material so received to the sample sensing module at the second speed, whereby a differential between the first speed and the second speed is operable to dynamically adjust a density of the input material provided by the second set of fiber movements. The sample preparation module further comprises a first electromagnetic radiation source disposed on a side adjacent the input material for directing a first beam of electromagnetic radiation toward the input material at a first location between the first set of fiber movements and the second set of fiber movements within the sample preparation module. The sample preparation module further comprises a first electromagnetic radiation sensor disposed on an opposite side of the input material from the first electromagnetic radiation source such that the first electromagnetic radiation sensor can receive first transmitted portions of the first beam of electromagnetic radiation that pass through the input material. The controller of this embodiment is further configured for receiving data signals from the first electromagnetic radiation sensor, sending control signals to the first electromagnetic radiation source, the first set of fiber movements, and the second set of fiber movements, and processing the data signals from the first electromagnetic radiation sensor and adjusting the control signals to the first set of fiber movements and the second set of fiber movements to provide a desired density of input material from the sample preparation module to the sample sensing module.

In one embodiment, the measurement instrument further comprises a hopper in the sample preparation module for holding the input material prior to delivery of the input material to the first set of fiber movements.

In one embodiment, the measurement instrument further comprises a first set of optics for delivering the second beam of electromagnetic radiation to the input material.

In one embodiment, the measurement instrument further comprises a second set of optics for delivering the second transmitted portion of the second beam of electromagnetic radiation to the second electromagnetic radiation sensor, and/or further comprising a third set of optics for delivering the third reflected portion of the second beam of electromagnetic radiation to the third electromagnetic radiation sensor.

In one embodiment, the measurement instrument further comprises a machine interface in the control module configured for communicating the fiber blend composition and/or the fiber blend ratio to at least one of prior processing equipment and post processing equipment. The machine interface in the control module can be configured for communicating the fiber blend composition and/or the fiber blend ratio to a prior fiber blending machine.

In one embodiment, the measurement instrument further comprises an information database in the control module for providing electromagnetic radiation transmission and reflectance data for a variety of fibers to the controller for use in determining fiber blend composition and/or fiber blend ratio. The electromagnetic radiation transmission and reflectance data can comprise data for manmade fibers and for natural fibers.

In one embodiment, the spectral illumination source comprise one or more of LED, halogen lamp, mercury vapor lamp, incandescent lamp, deuterium lamp, and xenon lamp.

In one embodiment, the second electromagnetic radiation sensor and/or the third electromagnetic radiation sensor comprise one or more of a spectrometer, photodiode, photodiode coupled with filter-wheel including band pass filters, photodiode array, each covered by narrow band filters, and hyper-spectral one-dimensional or two dimensional imagers.

In one embodiment, the second electromagnetic radiation sensor and/or the third electromagnetic radiation sensor comprises a plurality of electromagnetic radiation sensors disposed at differing positions along a surface of the input material in a direction perpendicular to the direction of movement of the input material.

In one embodiment, the second electromagnetic radiation sensor and/or the third electromagnetic sensor is movable along a surface of the input material in a direction perpendicular to the direction of movement of the input material.

In one embodiment, the fiber movements comprise at least one roller and/or at least one belt.

The method for identifying fiber blend composition and/or fiber blend ratio in an input material comprising fibers comprises the steps of:

a. drawing the input material at a second speed using a third set of fiber movements, b. directing a second beam of electromagnetic radiation toward the input material at a second location using a second electromagnetic radiation source disposed on an adjacent side of the input material, the second beam of electromagnetic radiation containing at least two clearly distinct wavelengths of the electromagnetic spectrum, c. receiving second transmitted portions of the second beam of electromagnetic radiation that pass through the input material using a second electromagnetic radiation sensor disposed on an opposite side of the input material opposite the second electromagnetic radiation source, and/or receiving third reflected portions of the second beam of electromagnetic radiation that reflect off of the input material using a third electromagnetic radiation sensor disposed on a same side of the input material as the second electromagnetic radiation source, wherein the second electromagnetic radiation sensor and/or the third electromagnetic radiation sensor are each configured to receive electromagnetic radiation at at least two clearly distinct wavelengths of the electromagnetic spectrum, d. receiving data signals from the second electromagnetic radiation sensor and/or the
third electromagnetic radiation sensor, e. sending control signals to the second electromagnetic radiation source and the third set of fiber movements, and f. processing the data signals from the second electromagnetic radiation sensor and/or the third electromagnetic radiation sensor to determine the fiber blend composition and/or the fiber blend ratio in the input material.

In one embodiment, the method according to the invention further comprises the following steps:

a. prior to step (a):
  i. receiving the input material with a first set of fiber movements moving at a first speed that is less than or equal to the second speed,
  ii. receiving the input material from the first set of fiber movements with a second set of fiber movements moving at the second speed, whereby a differential between the first speed and the second speed is operable to dynamically adjust a density of the input material provided by the second set of fiber movements,
  iii. directing a first beam of electromagnetic radiation toward the input material using a first electromagnetic radiation source disposed on a side adjacent the input material and at a first location between the first set of fiber movements and the second set of fiber movements,
  iv. receiving first transmitted portions of the first beam of electromagnetic radiation that pass through the input material using a first electromagnetic radiation sensor that is disposed on an opposite side of the input material from the first electromagnetic radiation source, b. in step (d), also receiving data signals from the first electromagnetic radiation sensor, c. in step (e), also sending control signals to the first electromagnetic radiation source, the first set of fiber movements, and the second set of fiber movements, and d. after step (e) and before step (f), processing the data signals from the first electromagnetic radiation sensor and adjusting the control signals to the first set of fiber movements and the second set of fiber movements to provide a desired density of input material to the second location.

In one embodiment, the method further comprises communicating the fiber blend composition and/or the fiber blend ratio to at least one of prior processing equipment and post processing equipment. The fiber blend composition and/or the fiber blend ratio can be communicated to a prior fiber blending machine.

In one embodiment, the second electromagnetic radiation sensor and/or the third electromagnetic radiation sensor comprises a plurality of electromagnetic radiation sensors disposed at differing positions along a surface of the input material in a direction perpendicular to the direction of movement of the input material.

In one embodiment, the method further comprises moving the second electromagnetic radiation sensor and/or the third electromagnetic radiation sensor along a surface of the input material in a direction perpendicular to the direction of movement of the input material.

BRIEF DESCRIPTION OF DRAWINGS

Further advantages of the invention are apparent by reference to the detailed description when considered in conjunction with the drawings, which are not to scale so as to more clearly show the details, wherein like reference numbers indicate like elements throughout the several views, and wherein.

DESCRIPTION OF EMBODIMENTS

Measurement Instrument

Figure 1:
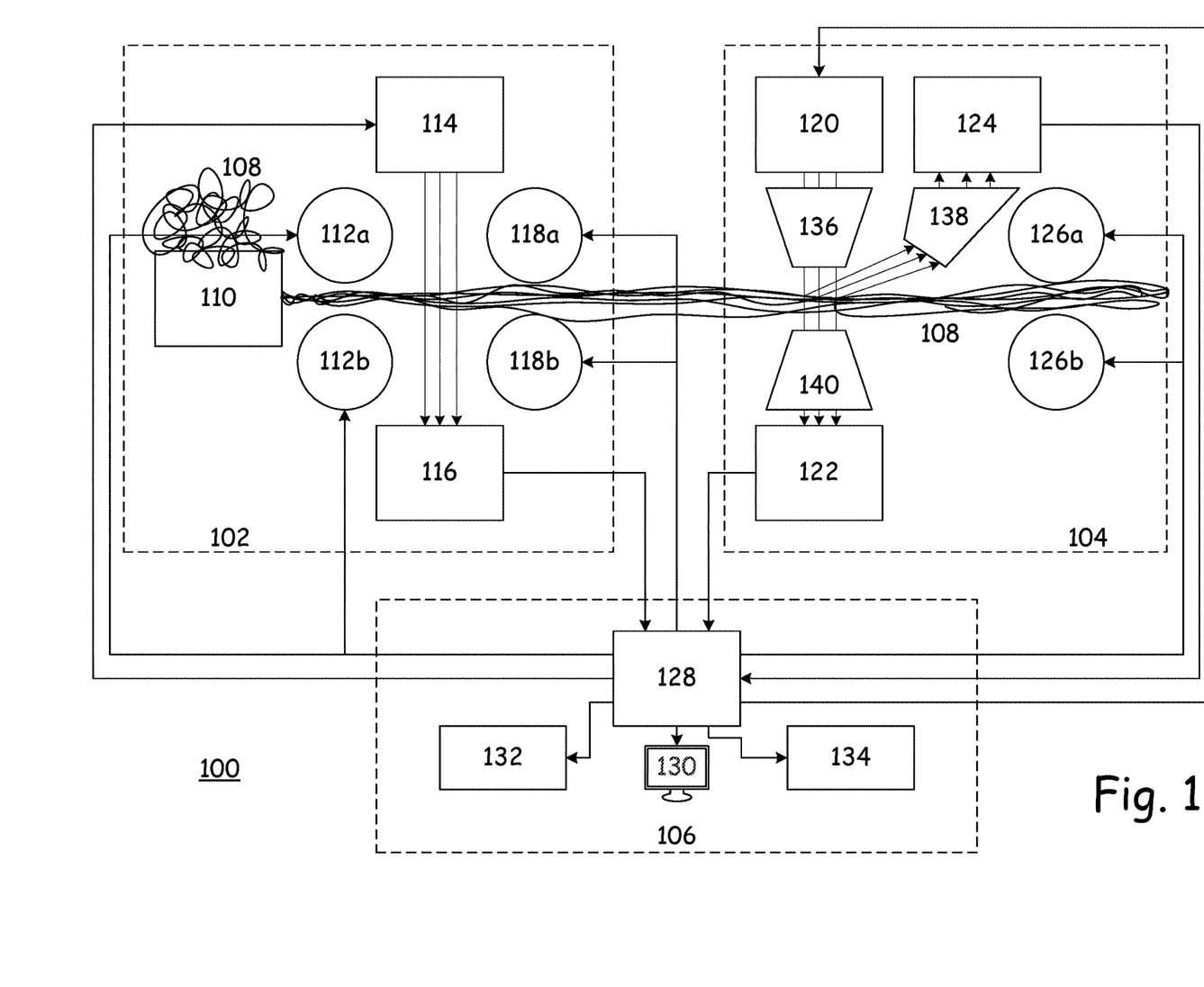
FIG. 1 is a functional block diagram of a measurement instrument according to an embodiment of the present invention.

With reference now to FIG. 1, there is depicted a functional block diagram of a blend ratio measurement instrument 100 according to an embodiment of the present invention. The measurement instrument 100 as described herein can be used for either online or offline measurement. The measurement instrument 100 includes the following modules:

Preparation module 102
Sensing module 104
Control module 106

FIG. 1 also depicts the main components of the measurement instrument 100, including the following:

Input material 108 for which blend composition and/or blend ratio is to be determined
Input hopper 110
Material preparation input fiber movement set 112
Material preparation illumination source 114
Material preparation sensor 116
Material preparation output fiber movement set 118
Spectral illumination source 120
Spectral illumination transmission sensor 122
Spectral illumination reflection sensor 124
Material sensing output fiber movement set 126
Signal processor and controller 128
Human user interface 130
Machine interface 132
Information database interface 134

Preparation Module

The preparation module 102 brings the fibrous input material 108 into the measurement instrument 100 and prepares the input material 108 for presentation to the sensors 116, 122, and 124, as described in more detail below. In one embodiment the input hopper 110 receives the input material 108 in batch form and provides it to the first set of input fiber movements 112, and in other embodiments the input material 108 is received by the first set of fiber movements 112 in a continuous feed, such as a sliver. The input material 108 can be received in various formats, such as bale, carding mat, sliver, and so forth. The preparation module 102 converts the input material 108 to a web format, such as a sliver, if it is not already presented as such.

In some embodiments, there are two presentation forms for the input material 108. One form is to present each fiber in the input material 108 to the sensors 116, 122, and 124 in an individualized form, and the other form is to present the input material 108 in the web format, which in some embodiments is of a consistent density, as described in more detail below. One way to achieve these various forms is by having variably-controlled drafting between the first set of fiber movements 112 and the second set of output fiber movements 118. By having the second set of fiber movements 118 rotating at a slightly faster speed than the first set of fiber movements 112, the input material 108 can be stretched thinner, allowing for the presentation of a thinner web of fibers. At a certain speed differential, the fibers can be presented in an almost individualized form. Thus, the density or thickness of the web of the input material 108 can be controlled in this manner.

The density of the input material 108 is monitored by evaluating the transmission level of electromagnetic radiation from the electromagnetic radiation source 114 through the web of input material 108 as received by the electromagnetic radiation sensor 116. The spectral range of emitted and sensed electromagnetic radiation can include, but is not limited to, ultraviolet, visible, and infrared.

Examples of the electromagnetic source 114 include, but are not limited to, one or more of LED, halogen lamp, mercury vapor lamp, incandescent lamp, deuterium lamp, and xenon lamp. Examples of the electromagnetic sensor 116 include, but are not limited to, one or more of a spectrometer, photodiode, photodiode coupled with filter-wheel including band pass filters, photodiode array, each covered by narrow band filters, and hyper-spectral one-dimensional or two dimensional imagers.

A closed-loop feedback control instrument in the controller 128 uses the transmission level information from the electromagnetic radiation sensor 116 to control the relative speed of the two sets of fiber movements 112 and 118, and thus the density of the web of input material 108. Thus, one important function of the preparation module 102 is to control the density of the web of input material 108 that is delivered to the sensing module 104, as next described.

Sensing Module

The sensing module 104 senses different fiber types and the different amounts of different fiber types that are present in the input material 108. This is accomplished by irradiating the web of input material 108 with electromagnetic radiation from the spectral illumination source 120, and then using at least one of a spectral transmission sensor 122 that detects the spectral transmission of the input material 108 and a spectral reflection sensor 124 that detects the spectral reflection of the input material 108. The spectral range of emitted and sensed electromagnetic radiation can include, but is not limited to, ultraviolet, visible, and infrared.

The spectral illumination source 120 is configured to emit electromagnetic radiation that contains at least two clearly distinct wavelengths of the electromagnetic spectrum. It is preferably a broadband electromagnetic source 120. Examples of the spectral illumination source 120 include, but are not limited to, one or more of LED, halogen lamp, mercury vapor lamp, incandescent lamp, deuterium lamp, and xenon lamp.

The electromagnetic sensors 122 and 124 are each configured to receive electromagnetic radiation at at least two clearly distinct wavelengths of the electromagnetic spectrum. The received wavelengths can be wavelengths emitted by the spectral illumination source 120, or can at least partly differ from them. Examples of the electromagnetic sensors 122 and 124 include, but are not limited to, one or more of a spectrometer, photodiode, photodiode coupled with filter-wheel including band pass filters, photodiode array, each covered by narrow band filters, and hyper-spectral one-dimensional or two dimensional imagers.

In some embodiments, the illumination from the source 120 is controlled by the controller 128 to be relatively uniform over the sensing area that is presented by the web of the input material 108. In some embodiments, all of the radiation that attains either the sensor 124 or the sensor 122 is captured and sensed. In one embodiment this is accomplished with the use of optical elements 136 that receive and shape the radiation delivered by the source 120, while other sets of optics 138 and 140 are used to capture the reflected and transmitted radiation and direct it to the sensors 122 and 124.

Figure 2:
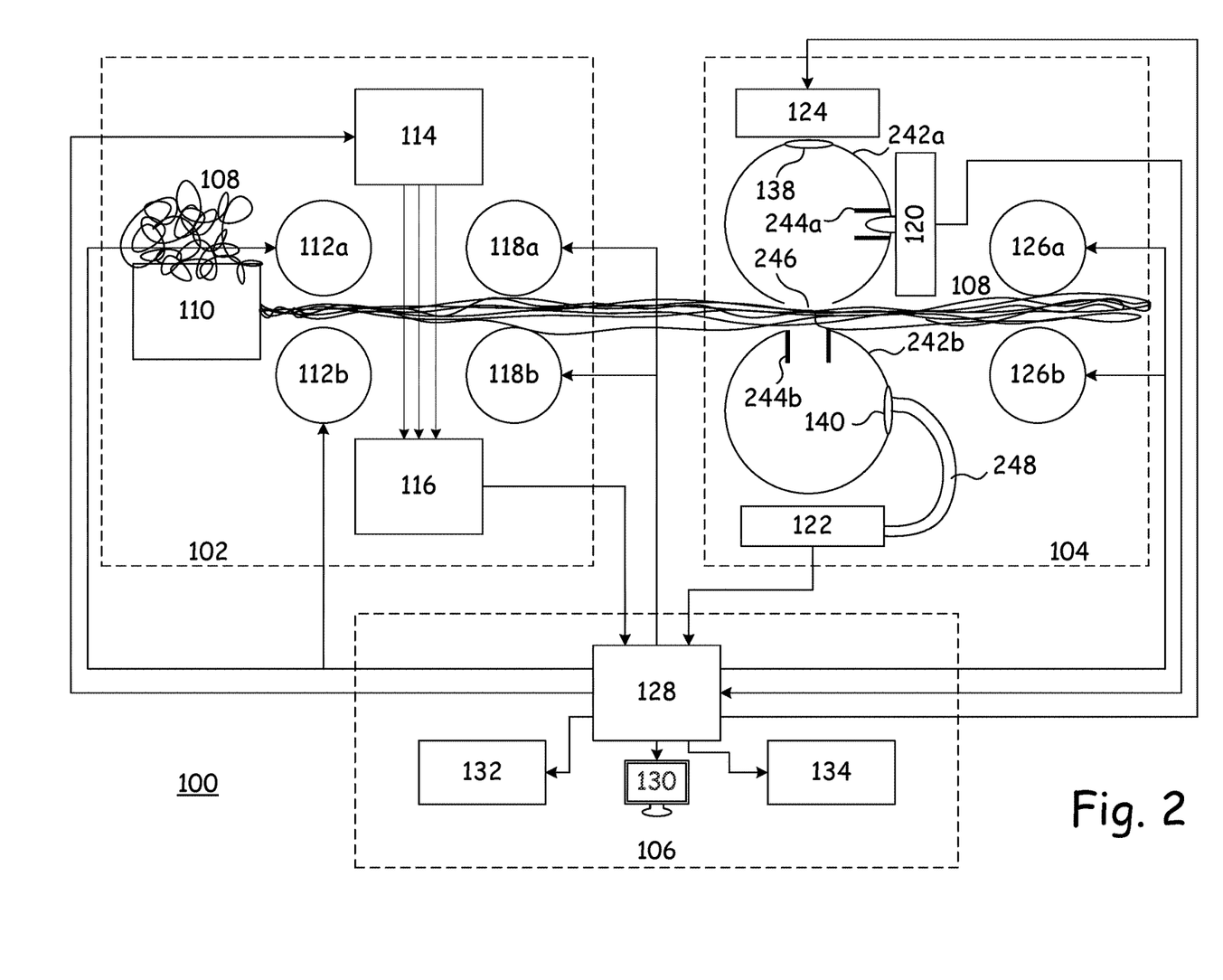
FIG. 2 is a functional block diagram of a measurement instrument according to another embodiment of the present invention.

Another embodiment uses an integrating sphere 242, as depicted in FIG. 2, which embeds the illumination source 120, thus providing a uniform illumination output. The integrating sphere is an optical component consisting of a hollow spherical cavity with its interior covered with a diffuse reflective coating that uniformly scatters the radiation. Electromagnetic radiation that is incident on any point on the inner surface is, by multiple scattering reflections, distributed equally to all other points on the sphere. The effects of the original direction of the electromagnetic radiation are thus reduced or even eliminated.

As depicted in FIG. 2, the integrating sphere 242a is used to both illuminate and receive the reflected illumination from the input material 108. The radiation enters the sphere 242a from the source 120, reflects around the sphere 242a, reflects from the input material 108 through the port 246, is eventually collected by the optics 138, and is then directly measured by the sensor 124. The baffle sets 244 prevent direct sensing of input radiation from the source 120.

As indicated above, in one embodiment, some of the radiation from the source 120 is transmitted through the input material 108 and enters the sphere 242b. Again, baffle set 244b prevents direct reception of the illumination by the collection optics 140. In this embodiment as depicted, the radiation received by the optics 140 is passed to the sensor 122 via an optical waveguide 248. In various embodiments, the same or different integrating spheres 242 can be used to capture reflected and transmitted signals, and optical waveguides can be used in either, none, or both of the integrating spheres 242.

In various embodiments, the sensing of the reflected or transmitted radiation is performed in either a static or dynamic mode, under the control of the controller 128. In static mode, a desired portion of the web of input material 108 is brought into the field of view of at least one of the sensors 122 and 124 and is stopped for measurement. In dynamic mode, the web of input material 108 continues to move while at least one of the sensors 122 and 124 operates at a sensing speed that, in one embodiment, is faster than the speed of the moving web of input material 108. The movement of the web of input material 108 through the sensing module 104 is maintained in one embodiment by the third set of fiber movements 126.

In some embodiments the fiber movement sets 112, 118, and 126 are rotating rollers, where either one or both of the rollers are driven. In other words, in some embodiments, one of the rollers in each set could be passive. In other embodiments the fiber movement sets 112, 118, and 126 are sets of belts, where again, one belt could be driven and the other belt could be passive, or both belts could be driven. In yet another embodiment, each set includes a single driven belt and on the other side of the input material 108 there is disposed a fixed or floating pressure plate.

Figure 6:
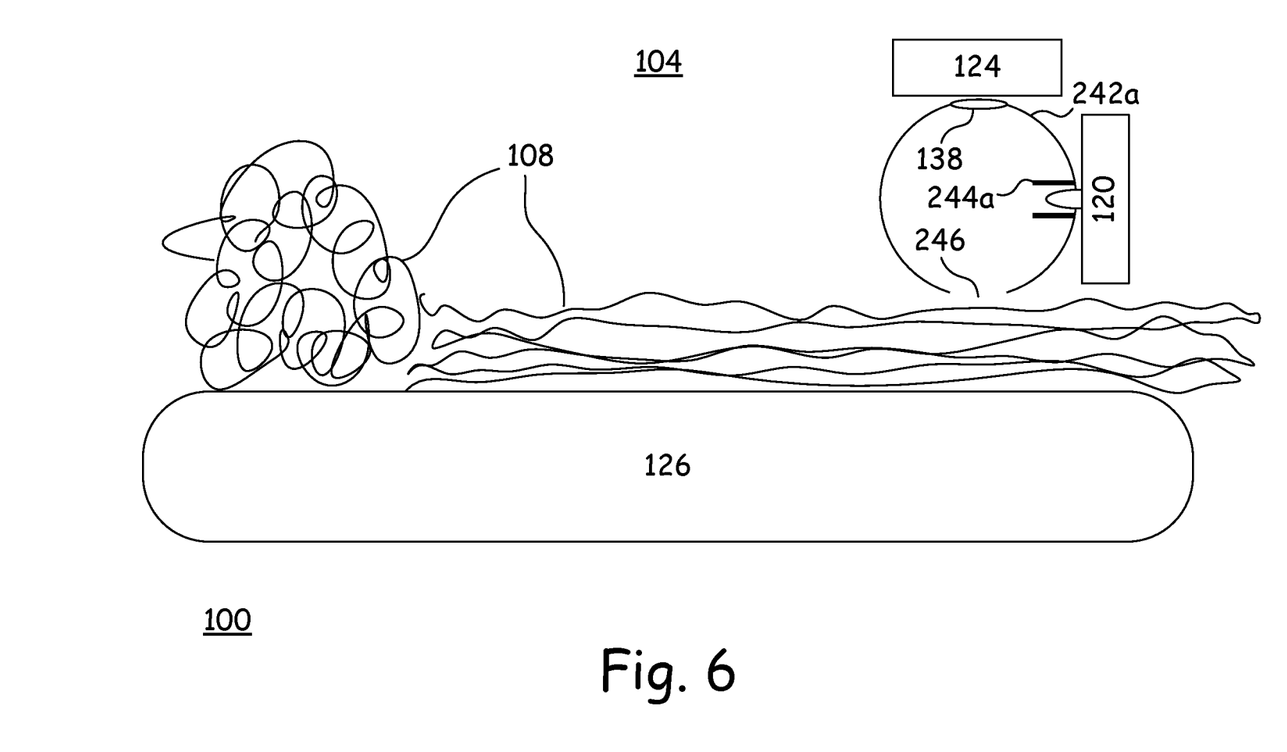
FIG. 6 is a functional block diagram of a measurement instrument using belts, according to another embodiment of the present invention.

FIG. 6 depicts a basic embodiment of the instrument 100, where a belt 126 draws the input material 108 past an integration sphere 242a, illumination source 120, and sensor 124, which operate in the manner as described elsewhere herein. Also in FIG. 6, there is no separate preparation module 102, just the sensing module 104. The control module 106 is not depicted in FIG. 6, but the control module 106 and control lines are used in such an embodiment.

Process/Control/Interface Module

In some embodiments, the control module 106 includes hardware to perform at least three functions, which are:

Process the gathered signals

Control the hardware

Interface with operators and other equipment

This is accomplished by the controller and signal processor 128, such as a personal computer or other computing device. The control functions include, but are not limited to, controlling the drafting operation between the two sets of fiber movements 112 and 118 in the preparation module 102, and controlling the movement of the web of input material 108 through the sensing instrument 104, such as with the fiber movements 126. It also processes the output of sensor 116, and provides feedback control to the drafting operation. Furthermore, it controls the spectral illumination source 120 and the input material fiber movement set 126, and processes the output of the sensors 122 and 124 via a measurement algorithm. The results of the measurement algorithm are communicated by the controller 128 to at least one of a human user interface 130 and a machine interface 132, which in some embodiments includes, but is not limited to, at least one of another type of textile machine.

Measurement Concept and Algorithm

The measurement concept is based on the understanding that each different type of material that fibers can be made of, and which may be included in the input material 108, has unique spectral transmissive and reflective signatures, which are used for detecting, differentiating, and measuring the amounts of the different fiber materials in a blend of such in the web that is tested.

In one embodiment, two types of blend ratio measurements can be used:

Blend.Ratioweight is the % of each unique fiber type in the blend by weight

Blend.Ratiocount is the % of each unique fiber type in the blend by number of fibers For a given single unique fiber material (only one component fiber), the spectral signature of the fiber material can be presented as:

$$F(\lambda_i) = R(\lambda_i) * S(\lambda_i) * P(\lambda_i) * D(\lambda_i) \qquad \text{Math. 1}$$

Where:
$F(\lambda_i)$ is the spectral response of the fiber material for a single range or multiple ranges of wavelengths where $\lambda_{min} < \lambda_i < \lambda_{min}=$, i=1, 2, . . . , n;
$R(\lambda_i)$ is the reflected or transmitting spectral response of the fiber material at wavelength $\lambda_i$, which is the only spectral response contributing to the spectral signature of the specific fiber material;
$S(\lambda_i)$ is the spectral response of the illumination source at wavelength $\lambda_i$;
$P(\lambda_i)$ is the spectral response reduced along the optical path, such as by one or more of air, fiber optics, lens, window, mirror, filter, and grating, at wavelength $\lambda_i$;
$D(\lambda_i)$ is spectral response of the sensor sensitivity at wavelength $\lambda_i$.

Similarly, for a given blend of material with several component fibers, the spectral signature of the blend material can be the sum of spectral signatures of the components, presented as:

$$B(\lambda_i) = \alpha (\Sigma_{j=1}^{m} k_j * F_j(\lambda_i)) \qquad \text{Math. 2}$$

Where:
$B(\lambda_i)$ is spectral response of the blend material for a single range or multiple ranges of wavelengths where $\lambda_{min} < \lambda_i < \lambda_{max}$, i=1, 2, . . . , n;
m is the number of different component fiber types in the blend;
$k_j$ is the percentage of each component fiber material type j in the blend;
$\alpha$ is a constant due to the overall spectral response variation of light source, sensor, or sample presentation;
$F_j(\lambda_i)$ is the spectral response of the component fiber material type J in the blend, which expression is in the equation Math. 1.

Figure 3:
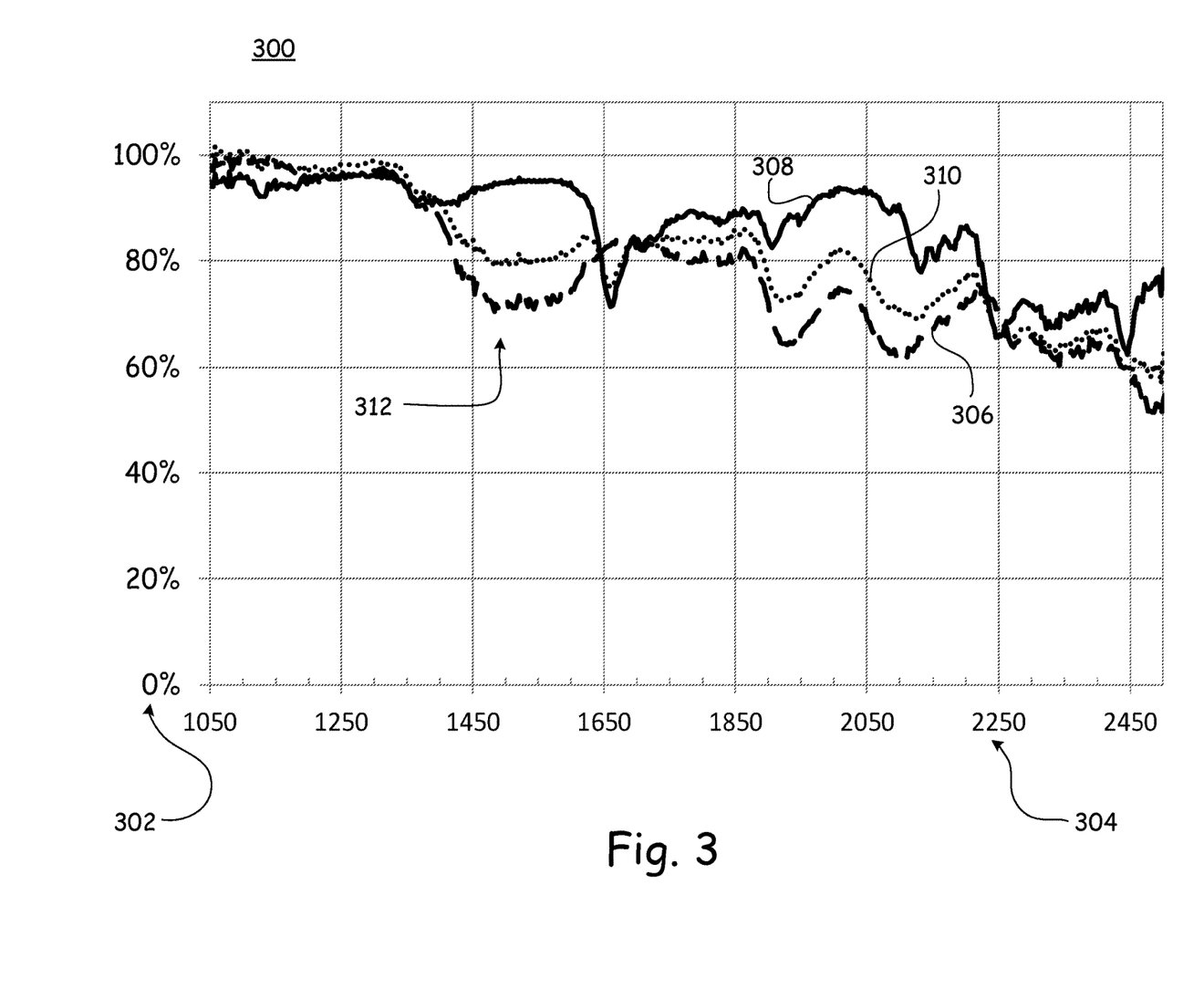
FIG. 3 is a plot of a spectral response for cotton, polyester, and a 50-50 cotton/polyester blend according to an embodiment of the present invention.

The instrument can be trained to determine $k_j$. The following example describes a method to determine $k_j$ for a two-component blend, such as a blend of cotton-polyester fibers. This method can be expanded to multi-components blends as well. FIG. 3 depicts a chart 300 for the relative spectral response 302 at different radiation wavelengths 304 (in nm) for natural cotton 306, polyester 308, and a 50-50 blend 310 by weight of cotton-polyester fibers. A careful analysis of these spectra points to a spectral region 312 where equation Math. 2 may be solved for $\lambda_{min}=1050$ nm$<\lambda_i<\lambda_{max}=2500$ nm to compute $k_j$ and thus Blend.Ratio$_{weight}$ or BlendRatio$_{count}$.

For a two-component blend, such as the polyester-cotton blend, equation Math. 2 can be expressed as:

$$B(\lambda_i) = c_1 * F_1(\lambda_i) + c_2 * F_2(\lambda_i) \qquad \text{Math. 3}$$

Where:
$\lambda_{min} < \lambda_i < \lambda_{max}=$, i=1, 2, . . . , n;
$c_1 = \alpha * k_1$;
$c_2 = \alpha * k_2$.

To measure the blend ratio of a two-component blend in one embodiment, 1) a calibration algorithm, and 2) a measurement algorithm are used. One embodiment of a calibration algorithm is given below.

1. The intent of the calibration algorithm is to convert $c_1$ and $c_2$ to a known blend ratio Blend.Ratio$_{weight}$ or Blend.Ratio$_{count}$ referred to as $p_{w1}$ in following equations.

2. Train the instrument by collecting spectral response of at least three samples:
   a. 100% component-1 (cotton in this case) referred to as $F_{1measured}(\lambda_i)$
   b. 100% component-2 (polyester in this case) referred to as $F_{2measured}(\lambda_i)$
   c. Blend with known blend ratio $p_{w1}$ (by weight or by fiber count) for component-1 and component-2 (cotton-polyester in this case) referred to as $B_{measured}(\lambda_i)$
3. Using a multiple regression method, compute $B_{predicted}(\lambda_i)$ using equation Math. 3, for $\lambda_{min}<\lambda_i<\lambda_{max}$, i=1, 2, . . . , n, to determine $c_1$ and $c_2$ to minimize $\Sigma_{i=1}^{n}(B_{predicted}(\lambda_i) - B_{measured}(\lambda_i))^2$.
4. The internal blend ratio prior to calibration is defined as:

$$p_{s1} = c_1/(c_1+c_2) \qquad \text{Math. 4}$$

$$p_{s2} = c_2/(c_1+c_2) \text{ or } p_{s2} = 1 - p_{s1} \qquad \text{Math. 5}$$

5. The calibration factor to convert internal blend ratio to BlendRatio$_{weight}$ or Blend.Ratio$_{count}$ is computed as:

$$SWC = (p_{s1}/(1-p_{s1})) * (1-p_{w1})/p_{w1} \qquad \text{Math. 6}$$

Where:
$p_{s1}$ is the internal blend ratio per equation Math. 4;
$p_{w1}$ is the known calibration blend ratio in Step 1;
SWC is a calibration factor for the two-component blend in blend ratio range of 0%<$p_{s1}$<100%.

Once SWC is determined via calibration, an unknown blend ratio of a given sample (assuming spectrally-similar component-1 and component-2 as used in calibration) can be computed as follows:

1. Capture the spectral response $B_{measured}(\lambda_i)$ of the blend sample with unknown blend ratio;
2. Using a multiple regression method, compute $B_{predicted}(\lambda_i)$ using equation Math. 3, for $\lambda_{min}<\lambda i<\lambda_{max}$, i=1, 2, . . . , n, to determine $c_1$ and $c_2$ to minimize $\Sigma_{i=1}^{n}(B_{predicted}(\lambda_i) - B_{measured}(\lambda_i))^2$.
3. Compute the internal $p_{s1}$ and $p_{s2}$ per equations Math. 4 and Math. 5;
4. The unknown blend ratio is computed by:

$$p_{w1} = p_{s1}(SWC - SWC * p_{s1} + p_{s1}) \qquad \text{Math. 7}$$

$$p_{w2} = 1 - p_{w1} \qquad \text{Math. 8}$$

Figure 4:
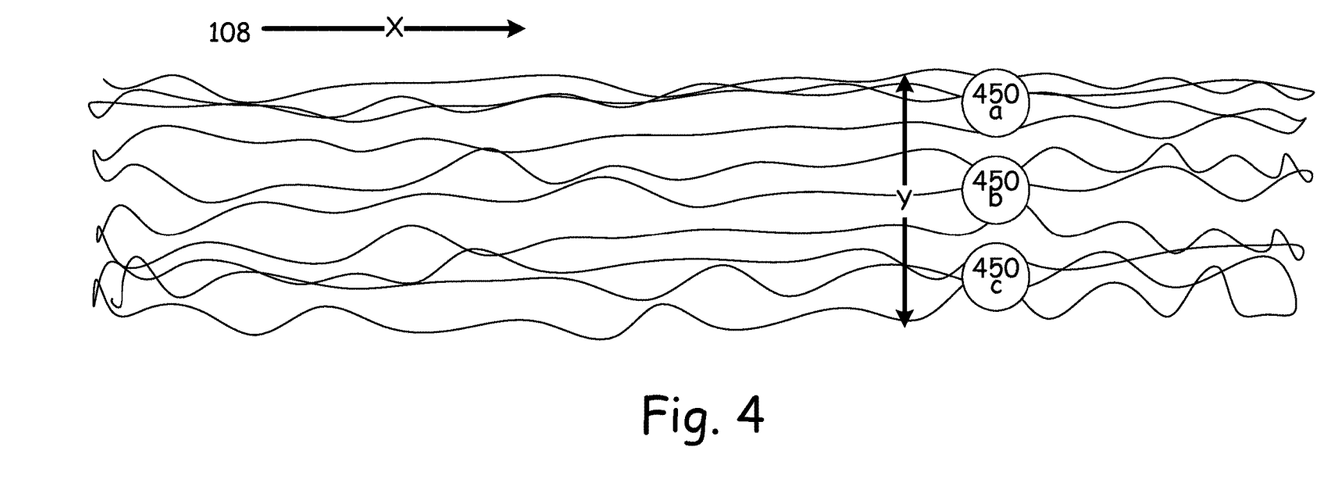
FIG. 4 is a functional block diagram of multiple sensors that are positioned within a mat of input material according to an embodiment of the present invention.

It is noted that the algorithm described above provides a blend ratio measurement for a single sensor field of view. The number of sensors, location of each sensor, and size of the sensor field of view depends on the width of the blend material, required blend ratio spatial resolution, required blend ratio uniformity spatial resolution, and cost considerations. For example, FIG. 4 depicts an embodiment of a measurement instrument 100 that contains input material 108 moving along an X direction through multiple fields of view of stationary multiple sensors 450a, 450b, and 450c. The multiple sensors 450a, 450b, and 450c are disposed at differing positions along a surface of the input material 108 in a Y direction, which is perpendicular to the X direction, so as to cover at least part of and preferably the whole width of the input material 108.

Figure 5:
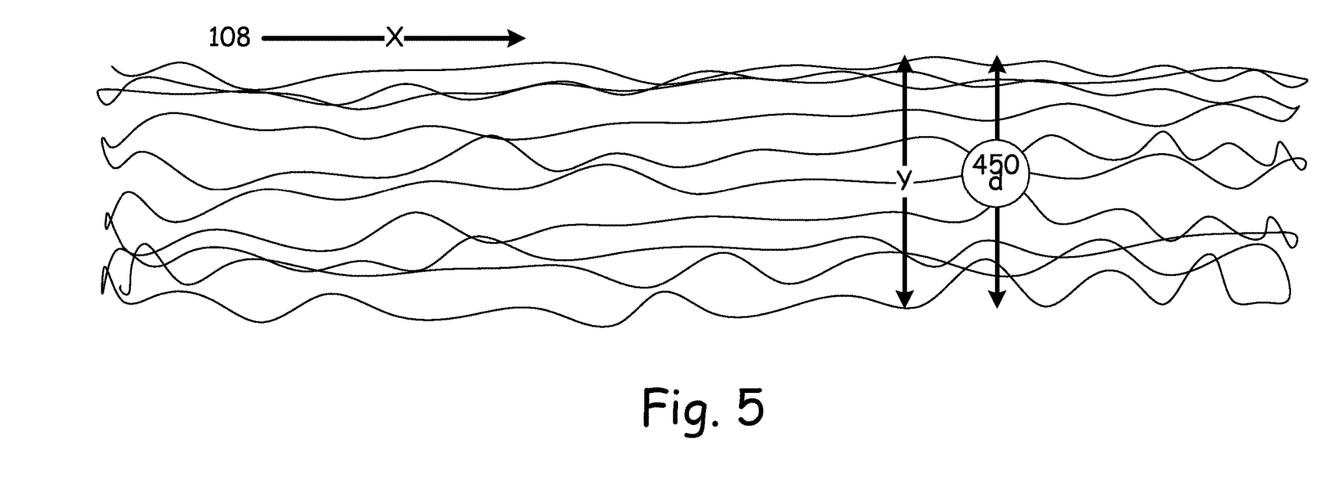
FIG. 5 is a functional block diagram of a moving sensor that is positioned with a mat of input material according to another embodiment of the present invention.

Alternately, FIG. 5 shows yet another embodiment of a measurement instrument 100 that contains input material 108 moving along an X direction through one field of view of a single sensor 450d, which in some embodiments is a movable sensor 450d. Simultaneously, the input material 108 can also be sensed along the Y direction by either moving the sensor 450d or moving the input material 108 in the Y direction along a surface of the input material 108. The movement in the Y direction is such that at least part of and preferably the whole width of the input material 108 is covered. In both embodiments, the result is an array of position-dependent blend ratio measurements that relates to different portions of the input material 108. Thus, the position-stamped blend ratio can be presented as:

$$p_k(j) \qquad \text{Math. 9}$$

Where:
k is the index of the $k^{th}$ component, k=1, 2, ..., l;
i is the position index of X direction, i=1, 2, ..., m;
j is the position index of Y direction, j=1, 2, ..., n.

For the embodiment of FIG. 4, n=3 if three sensors 450a, 450b, and 450c are present. For the embodiment of FIG. 5, the data can be either one-dimensional or two-dimensional, that is n=1 or n>1.

Based on the testing data $p_k(i,j)$ in equation Math. 9, further statistical analysis can be done to reveal spatial distribution of blend ratio along X direction and Y direction. Thus, using the testing data $p_k(i,j)$ in equation Math 9, the further calculations and position values can be presented as:

|       | $Y_1$      | $Y_2$      | ... | $Y_n$      | Avg_Y    | SD_Y      |
|-------|------------|------------|-----|------------|----------|-----------|
| $X_1$ | $p_k(1,1)$ | $p_k(1,2)$ | ... | $p_k(1,n)$ | $py_k(1)$ | $dpy_k(1)$ |
| $X_2$ | $p_k(2,1)$ | $p_k(2,2)$ | ... | $p_k(2,n)$ | $py_k(2)$ | $dpy_k(2)$ |
| .     | .          | .          |     | .          | .        | .         |
| .     | .          | .          |     | .          | .        | .         |
| .     | .          | .          |     | .          | .        | .         |
| $X_m$ | $p_k(m,1)$ | $p_k(m,2)$ | ... | $p_k(m,n)$ | $py_k(m)$ | $dpy_k(m)$ |
| Avg_X | $px_k(1)$  | $px_k(2)$  | ... | $px_k(n)$  | $pxy_k$  |           |
| SD_X  | $dpx_k(1)$ | $dpx_k(2)$ | ... | $dpx_k(n)$ |          | $dpxy_k$  |

Where:
k is the index of the $k^{th}$ component, k=1, 2, ..., l;
$px_k(j)$, j=1, 2, ..., n, is the average of test points along X direction with Y direction index of j;
$dpx_k(j)$, j=1, 2, ..., n, is the standard deviation of test points along X direction with Y direction index of j;
$py_k(i)$, i=1, 2, ..., m, is the average of test points along Y direction with X direction index of i;
$dpy_k(i)$, i=1, 2, ..., m, is the standard deviation of test points along Y direction with X direction index of i;
$pxy_k$ is the average of all test points of the sample;
$dpxy_k$ is the standard deviation of all test points of the sample.

$pxy_k$ reveals the overall blend ratio of the sample, and $dpxy_k$ reveals the overall blend ratio variation (uniformity) of the sample. $px_k(j)$, j=1, 2, ..., n, reveals the blend ratio distribution along the Y direction, but $dpx_k(j)$, j=1, 2, ..., n, reveals the blend ratio variation (uniformity) along the X direction. Similarly, $py_k(i)$, i=1, 2, ..., m, reveals the blend ratio distribution along the X direction, but $dpy_k(i)$, i=1, 2, ..., m, reveals the blend ratio variation (uniformity) along the Y direction.

Plots of $p_k(i,j)$, $px_k(j)$ and $py_k(i)$, where i=1, 2, ..., m and j=1, 2, ..., n, graphically reveal the blend ratio distribution characters of the sample. For example, drawing a sliver of blended fibers usually has a stripe structure, so that the blend ratio varies in a certain period across the sliver (Y direction). The size of the blend ratio period across the sliver and blend variation levels along and across the sliver are valuable information for spinning process quality control.

The measurement instrument 100 can determine the blend ratio, assuming the main components of the blends are known in advance. Yet another capability of the measurement instrument 100 is to predict the material type of an unknown single-component fiber and multi-component blend. A spectral signature of an unknown material can be compared to a single component or component combinations in a database, and the closest match can be found.

The component identification algorithm for an unknown material includes three major parts described in the following.

The first part is seeding, which includes collecting and maintaining the spectral signatures of all single components of interest throughout time for different fibers and materials. This can be achieved by either obtaining the spectral signatures from external sources (such as fiber manufacturers) or using the described instrument (during the training process) to create the spectral signatures of all single components of interest. These spectral signatures are maintained in a database, which can be connected to the controller 128 via the information database interface 134 as shown in FIG. 1.

The second part is searching, which includes searching for a match between the spectral signature of the unknown material and every possible single-component/multi-component blend using the linear combination expression in equation Math 2, which can also be expressed as:

$$B(\lambda_i) = \sum_{j=1}^{m} c_j * F_j(\lambda_i) \qquad \text{Math. 10}$$

Where:
$\lambda_{min} < \lambda_i < \lambda_{max}$, i=1, 2, ..., n;
m=1, single-component;
m=2, 3, ..., M, multi-component blend, where M is the number of components in the calibration file.

Take, for example, the case where there are only four components (M=4) of interest, such as cotton, polyester, acrylic, and viscose. In this case, the total number of possible combinations is 15, which can be indexed as (1), (2), (3), (4), (1, 2), (1, 3), (1, 4), (2, 3), (2, 4), (3, 4), (1,2,3), (1,2,4), (1,3,4), (2,3,4), (1,2,3,4).

The third part is matching criteria, which is a quantified measure of how close an unknown material is to the outcome of the searching process described in the previous step. Various mathematical goodness-of-fit measures, such as a determination coefficient ($R^2$) or sum of squared errors (SSE), may be used to assess the match for every possible linear combination of components. In the case where no component combination has a goodness-of-fit calculation within the criterial ranges, the unknown material may have a component that is not included in the database of known materials (first part); otherwise, the best fit should reveal the component combinations for the unknown material.

The methods described above can be implemented in the controller/signal processor 128, as depicted in FIGS. 1 and 2. However, the implementation does not depend on a specific embodiment of the blend ratio measurement instrument 100 according to the invention.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A measurement instrument for identifying at least one of fiber blend composition and fiber blend ratio in an input material comprising fibers, the measurement instrument comprising:
   a. a sample sensing module comprising:
      i. a third set of fiber movements for drawing the input material through the sample sensing module at a second speed,
      ii an electromagnetic radiation source disposed on an adjacent side of the input material for directing a beam of electromagnetic radiation toward the input material at a second location within the sample sensing module, the beam of electromagnetic radiation containing at least two clearly distinct wavelengths of the electromagnetic spectrum,
      iii. at least one of an electromagnetic radiation transmission sensor disposed on an opposite side of the input material opposite the electromagnetic radiation source such that the electromagnetic radiation transmission sensor receives transmitted portions of the beam of electromagnetic radiation that pass through the input material, and an electromagnetic radiation reflection sensor disposed on a same side of the input material as the electromagnetic radiation source such that the electromagnetic radiation reflection sensor receives reflected portions of the beam of electromagnetic radiation that reflect off of the input material, wherein at least one of the electromagnetic radiation transmission sensor and the electromagnetic radiation reflection sensor are each configured to receive electromagnetic radiation at least two clearly distinct wavelengths of the electromagnetic spectrum, and
   b. a control module comprising a controller configured for:
      i. receiving data signals from at least one of the electromagnetic radiation transmission sensor and the electromagnetic radiation reflection sensor,
      ii. sending control signals to the electromagnetic radiation source and the third set of fiber movements, and
      iii. processing the data signals from at least one of the electromagnetic radiation transmission sensor and the electromagnetic radiation reflection sensor to determine at least one of the fiber blend composition and the fiber blend ratio in the input material.

2. The measurement instrument of claim 1, further comprising:
   a. a sample preparation module for receiving and preparing the input material, the sample preparation module comprising:
      i. a first set of fiber movements for receiving the input material and providing the input material at a first speed that is less than or equal to the second speed,
      ii. a second set of fiber movements for receiving the input material from the first set of fiber movements at the first speed and providing the input material so received to the sample sensing module at the second speed, whereby a differential between the first speed and the second speed is operable to dynamically adjust a density of the input material provided by the second set of fiber movements,
      iii. a material preparation electromagnetic radiation source disposed on a side adjacent the input material for directing a beam of electromagnetic radiation toward the input material at a first location between the first set of fiber movements and the second set of fiber movements within the sample preparation module, and
      iv. a material preparation sensor disposed on an opposite side of the input material from the material preparation electromagnetic radiation source such that the material preparation sensor receives transmitted portions of the beam of electromagnetic radiation that pass through the input material, and
   b. the controller further configured for:
      i. receiving data signals from the material preparation sensor,
      ii. sending control signals to the material preparation electromagnetic radiation source, the first set of fiber movements, and the second set of fiber movements, and
      iii. processing the data signals from the material preparation sensor and adjusting the control signals to the first set of fiber movements and the second set of fiber movements to provide a desired density of input material from the sample preparation module to the sample sensing module.

3. The measurement instrument of claim 2, further comprising a hopper in the sample preparation module for holding the input material prior to delivery of the input material to the first set of fiber movements.

4. The measurement instrument of claim 1, further comprising a first set of optics for delivering the beam of electromagnetic radiation to the input material.

5. The measurement instrument of claim 1, further comprising at least one of a second set of optics for delivering the transmitted portion of the beam of electromagnetic radiation to the electromagnetic radiation transmission sensor, and a third set of optics for delivering the reflected portion of the beam of electromagnetic radiation to the electromagnetic radiation reflection sensor.

6. The measurement instrument of claim 1, further comprising a machine interface in the control module configured for communicating at least one of the fiber blend composition and the fiber blend ratio to at least one of prior processing equipment and post processing equipment.

7. The measurement instrument of claim 6, wherein the machine interface in the control module is configured for communicating at least one of the fiber blend composition and the fiber blend ratio.

8. The measurement instrument of claim 1, further comprising an information database interface in the control module for providing electromagnetic radiation transmission and reflectance data for a variety of fibers to the controller for use in determining at least one of fiber blend composition and fiber blend ratio.

9. The measurement instrument of claim 8, wherein the electromagnetic radiation transmission and reflectance data comprise data for manmade fibers and for natural fibers.

10. The measurement instrument of claim 1, wherein the electromagnetic radiation source comprises one or more of LED, halogen lamp, mercury vapor lamp, incandescent lamp, deuterium lamp, and xenon lamp.

11. The measurement instrument of claim 1, wherein at least one of the electromagnetic radiation transmission sensor and the electromagnetic radiation reflection sensor comprise at least one of a spectrometer, photodiode, photodiode coupled with filter-wheel including band pass filters, photodiode array, each covered by narrow band filters, and at least one of hyper-spectral one-dimensional and two dimensional imagers.

12. The measurement instrument of claim 1, wherein at least one of the electromagnetic radiation transmission sensor and the electromagnetic radiation reflection sensor comprises a plurality of electromagnetic radiation sensors disposed along a surface of the input material at differing positions in a direction (Y) perpendicular to the direction of movement (X) of the input material.

13. The measurement instrument of claim 1, wherein at least one of the electromagnetic radiation transmission sensor and the electromagnetic radiation reflection sensor is movable along a surface of the input material in a direction (Y) perpendicular to the direction of movement (X) of the input material.

14. The measurement instrument of claim 1, wherein the fiber movements comprise at least one of at least one roller and at least one belt.

15. A method for identifying at least one of fiber blend composition and fiber blend ratio in an input material comprising fibers, the method comprising the steps of:
 a. drawing the input material at a second speed using a third set of fiber movements,
 b. directing a beam of electromagnetic radiation toward the input material at a second location using an electromagnetic radiation source disposed on an adjacent side of the input material, the beam of electromagnetic radiation containing at least two clearly distinct wavelengths of the electromagnetic spectrum,
 c. receiving at least one of transmitted portions of the beam of electromagnetic radiation that pass through the input material using an electromagnetic radiation transmission sensor disposed on an opposite side of the input material opposite the electromagnetic radiation source, and reflected portions of the beam of electromagnetic radiation that reflect off of the input material using an electromagnetic radiation reflection sensor disposed on a same side of the input material as the electromagnetic radiation source, wherein at least one of the electromagnetic radiation transmission sensor and the electromagnetic radiation reflection sensor is configured to receive electromagnetic radiation at at least two clearly distinct wavelengths of the electromagnetic spectrum,
 d. receiving data signals from at least one of the electromagnetic radiation transmission sensor and the electromagnetic radiation reflection sensor,
 e. sending control signals to the electromagnetic radiation source and the third set of fiber movements, and
 f. processing the data signals from at least one of the electromagnetic radiation transmission sensor and the electromagnetic radiation reflection sensor to determine at least one of the fiber blend composition and the fiber blend ratio in the input material.

16. The method of claim 15, further comprising the following steps:
 a. prior to step (a):
  i. receiving the input material with a first set of fiber movements moving at a first speed that is less than or equal to the second speed,
  ii. receiving the input material from the first set of fiber movements with a second set of fiber movements moving at the second speed, whereby a differential between the first speed and the second speed is operable to dynamically adjust a density of the input material provided by the second set of fiber movements,
  iii. directing a beam of electromagnetic radiation toward the input material using a material preparation electromagnetic radiation source disposed on a side adjacent the input material and at a first location between the first set of fiber movements and the second set of fiber movements,
  iv. receiving transmitted portions of the beam of electromagnetic radiation that pass through the input material using a material preparation sensor that is disposed on an opposite side of the input material from the material preparation electromagnetic radiation source,
 b. in step (d), also receiving data signals from the material preparation sensor,
 c. in step (e), also sending control signals to the material preparation electromagnetic radiation source, the first set of fiber movements, and the second set of fiber movements, and
 d. after step (e) and before step (f), processing the data signals from the material preparation sensor and adjusting the control signals to the first set of fiber movements and the second set of fiber movements to provide a desired density of input material to the second location.

17. The method of claim 15, further comprising communicating at least one of the fiber blend composition and the fiber blend ratio to at least one of prior processing equipment and post processing equipment.

18. The method of claim 17, wherein at least one of the fiber blend composition and the fiber blend ratio is communicated.

19. The method of claim 15, wherein at least one of the electromagnetic radiation transmission sensor and the electromagnetic radiation reflection sensor comprises a plurality of electromagnetic radiation sensors disposed at differing positions along a surface of the input material in a direction (Y) perpendicular to the direction of movement (X) of the input material.

20. The method of claim 15, further comprising moving at least one of electromagnetic radiation transmission sensor and the electromagnetic radiation reflection sensor along a surface of the input material in a direction (Y) perpendicular to the direction of movement (X) of the input material.

\* \* \* \* \*